United States Patent
Sardo et al.

(10) Patent No.: US 11,553,721 B2
(45) Date of Patent: *Jan. 17, 2023

(54) PROCESS FOR TREATMENT BY AT LEAST ONE MODERATELY VOLATILE BIOCIDAL AND/OR PLANT-PROTECTION PRODUCT, CORRESPONDING TREATMENT ASSEMBLY AND STORAGE ASSEMBLY

(71) Applicant: XEDA INTERNATIONAL S.A., Saint Andiol (FR)

(72) Inventors: Alberto Sardo, Chateaurenard (FR); Stefano Sardo, Chateaurenard (FR); Laura Paitel, Le Pontet (FR)

(73) Assignee: XEDA INTERNATIONAL S.A., Saint Andiol (FR)

( * ) Notice: Subject to any disclaimer, the term of this patent is extended or adjusted under 35 U.S.C. 154(b) by 201 days.

This patent is subject to a terminal disclaimer.

(21) Appl. No.: 16/496,005

(22) PCT Filed: Mar. 21, 2018

(86) PCT No.: PCT/EP2018/057143
§ 371 (c)(1),
(2) Date: Sep. 20, 2019

(87) PCT Pub. No.: WO2018/172402
PCT Pub. Date: Sep. 27, 2018

(65) Prior Publication Data
US 2020/0060300 A1    Feb. 27, 2020

(30) Foreign Application Priority Data
Mar. 22, 2017  (FR) ..................... 17 52368

(51) Int. Cl.
*A23B 9/22* (2006.01)
*A01N 25/18* (2006.01)
(Continued)

(52) U.S. Cl.
CPC ............. *A23B 9/22* (2013.01); *A01N 25/18* (2013.01); *A23L 3/3445* (2013.01); *A23L 3/34095* (2013.01); *A23V 2002/00* (2013.01)

(58) Field of Classification Search
CPC ...... A23L 3/3445; A23L 3/34095; A61L 2/22; A61L 9/14; A61L 2/20; A61L 2/24;
(Continued)

(56) References Cited

U.S. PATENT DOCUMENTS

| 5,451,248 A | 9/1995 | Sadkowski et al. |
| 7,638,114 B1 | 12/2009 | Schur |

(Continued)

FOREIGN PATENT DOCUMENTS

| CN | 1084590 C | 3/1994 |
| CN | 104582809 B | 4/2015 |

(Continued)

OTHER PUBLICATIONS

Search Report of corresponding French Application No. FR 17 52368—2 pages (dated Jul. 21, 2017).
(Continued)

*Primary Examiner* — Subbalakshmi Prakash
(74) *Attorney, Agent, or Firm* — Knobbe, Martens, Olson & Bear, LLP

(57) ABSTRACT

The process includes a treatment step during which a liquid containing a biocidal and/or plant-protection product or a mixture of biocidal and/or plant-protection products is evaporated and injected into the internal atmosphere of premises, the liquid being evaporates at a temperature of less than 50° C., the product vapour concentration in the internal atmosphere of the premises being kept at greater than 10% of a saturation concentration of the vapour of said product in said atmosphere at said temperature for a saturation duration of greater than 12 hours.

15 Claims, 2 Drawing Sheets

(51) Int. Cl.
*A23L 3/3409* (2006.01)
*A23L 3/3445* (2006.01)

(58) Field of Classification Search
CPC ..... A61L 9/032; A61L 2202/25; A01N 25/18; A01N 65/00; A23B 9/18; A23B 9/22; A23V 2002/00
USPC .......................................................... 426/320
See application file for complete search history.

(56) References Cited

U.S. PATENT DOCUMENTS

| | | |
|---|---|---|
| 2008/0251215 A1 | 10/2008 | Chen |
| 2013/0341809 A1 | 12/2013 | Sardo |
| 2014/0200137 A1 | 7/2014 | Forsythe et al. |
| 2016/0030615 A1 | 2/2016 | Sardo |
| 2019/0159470 A1 | 5/2019 | Sardo et al. |
| 2021/0000127 A1 | 1/2021 | Sardo et al. |

FOREIGN PATENT DOCUMENTS

| | | |
|---|---|---|
| EP | 0452512 A1 | 10/1991 |
| EP | 2918336 A1 | 9/2015 |
| FR | 1338080 A | 9/1963 |
| FR | 2441812 A1 | 6/1980 |
| FR | 2964887 A1 | 3/2012 |
| FR | 2992225 B1 | 5/2015 |
| GB | 397848 A | 8/1933 |
| GB | 476272 A | 12/1937 |
| GB | 782848 A | 9/1957 |
| GB | 1054405 A | 1/1967 |
| JP | S61-118269 U | 7/1986 |
| JP | 2015527897 A | 9/2015 |
| RU | 2084115 C1 | 7/1997 |
| RU | 2138939 C1 | 10/1999 |
| RU | 2360743 C2 | 7/2009 |
| WO | WO 00/32063 A1 | 6/2000 |
| WO | WO 2007/026363 A2 | 3/2007 |
| WO | WO 2012/081015 A1 | 6/2012 |
| WO | WO 2014/001201 A1 | 1/2014 |
| WO | WO 2017/042072 A1 | 3/2017 |
| WO | WO 2017/220587 A1 | 12/2017 |

OTHER PUBLICATIONS

International Search Report of International Application No. PCT/EP2018/057143—4 pages (dated Apr. 24, 2018).
Search Report of corresponding PCT Application No. PCT/EP2017/065102—2 pages (dated Sep. 4, 2017).

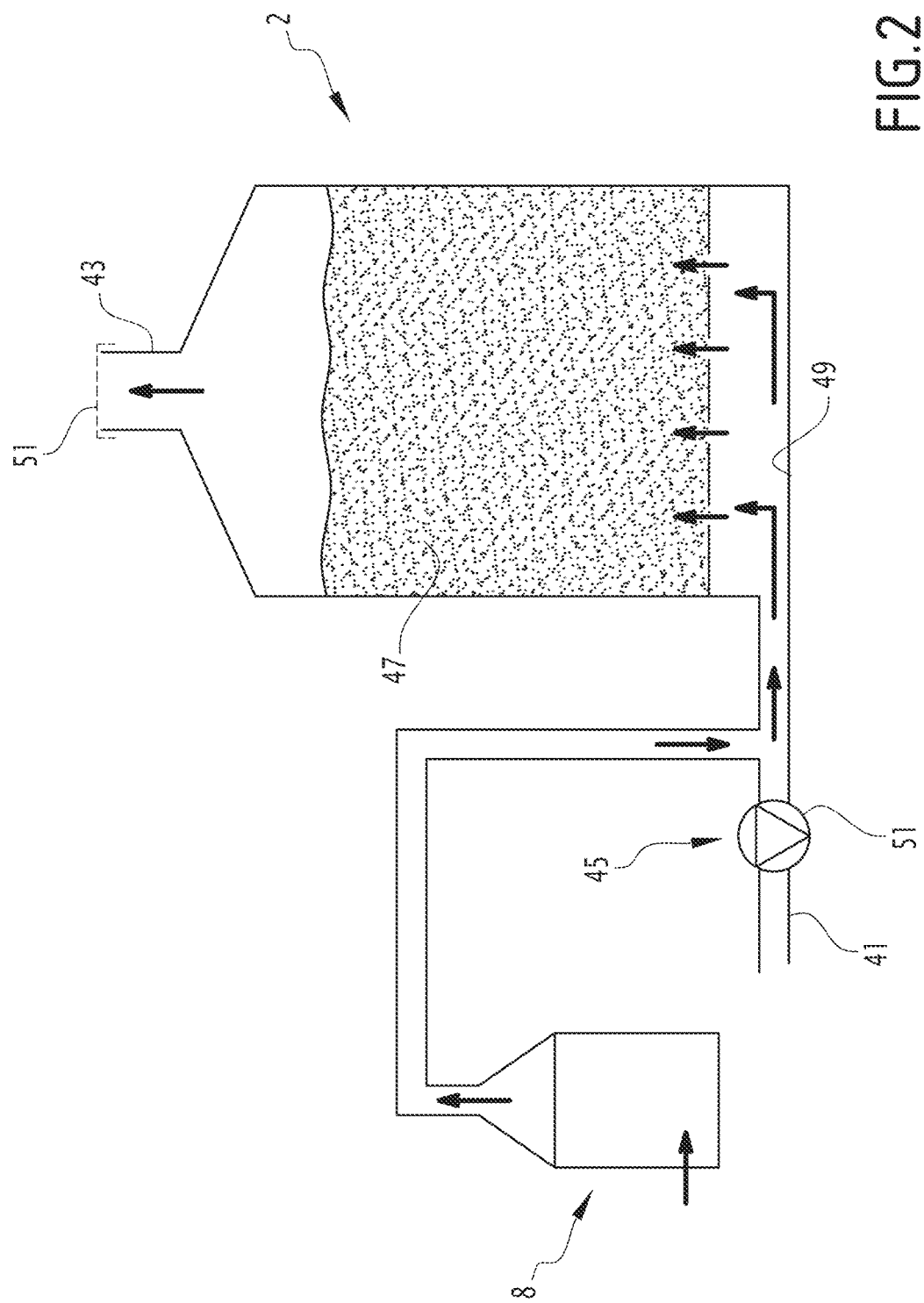

PROCESS FOR TREATMENT BY AT LEAST ONE MODERATELY VOLATILE BIOCIDAL AND/OR PLANT-PROTECTION PRODUCT, CORRESPONDING TREATMENT ASSEMBLY AND STORAGE ASSEMBLY

FIELD

The present invention concerns treatments with moderately volatile biocidal and/or plant-protection products, in particular to improve the storage of plant products such as cereals or for the disinfection of premises.

More specifically, the invention in a first aspect concerns a treatment process with at least one moderately volatile biocidal and/or plant-protection product.

BACKGROUND

It is known that some synthetic volatile products or of natural origin e.g. essential oils have biocidal or plant-protection properties of interest. In particular, they are used to treat plant products to improve the preservation thereof.

The techniques used up until now to apply these products to plants are the following:
- immersion of the plant products in a hot or cold aqueous dispersion containing the product;
- spraying the premises e.g. plant storage chambers, for sanitization;
- micro-misting when plant products enter the storage chambers.

The quantities of applied products are high and may lead to large concentrations in plant products.

Also, the grain sterilization processes currently used are based on spraying grain, on entry into silos, with highly toxic products; generally organophosphorus products. In the event of major insect attack during storage, the seeds are then treated with a gaseous product or fumigated volatile product. The products routinely used for this sterilization are phosphine, methyl bromide or ethyl formate. The treatment products used when entering storage or during storage are highly toxic and at times scarcely effective, notably on account of resistance-related problems.

SUMMARY

There is therefore a need for a treatment process that can be used to apply moderately volatile products of natural origin e.g. essential oils or synthetic products having the same volatility characteristics, and which has excellent efficacy for the protection of plant products and/or sanitization of premises, in particular premises intended for the storage of plant products.

For this purpose, the invention relates to a treatment process with at least one moderately volatile, biocidal and/or plant-protection product having a boiling point of between 150 and 280° C., the method comprising a treatment step at which a liquid containing a biocidal and/or plant-protection product or product mixture is evaporated and injected into the inner atmosphere of premises, the liquid being evaporated at a temperature lower than 50° C., the product vapour concentration in the inner atmosphere of the premises being held at more than 10% of the saturation concentration of the vapour of said product in said atmosphere at said temperature for a saturation time of more than 12 hours.

The applicant is convinced that solely vapours of moderately volatile, biocidal and/or plant-protection products are active, particularly having fungicidal, bactericidal and insecticidal action. The liquids containing moderately volatile, biocidal and/or plant-protection products are only active as vapour source.

As a result, the biocidal and/or plant-protection effect is maximum when the vapour concentration is held at a high value in the atmosphere of the premises to be treated.

To obtain best results, it is essential that these products should be used in vapour form. Only vapour is immediately active and will have the capability to treat the volume of air and enter into the bulk of the stored plant products (grain in silos, fruit in pallet boxes, heaped potatoes) and to obtain in-depth treatment of the premises walls.

The use of hot vaporisation to reach high vapour concentrations in the atmosphere is strongly ill-advised. Either the saturation concentration is not reached, or it is exceeded with resulting re-condensation of the vapours to liquid when they cool down after injection into the inner atmosphere of the premises, in particular on cold surfaces. To be sure of obtaining a high vapour concentration, large quantities of products would therefore need to be injected which can lead to high concentrations on plant products and would make these products phytotoxic, at the same time entailing a much higher consumption of biocidal and/or plant-protection product than with cold evaporation.

Thermal fogging raises similar problems. The product is injected in the liquid state in the form of misted droplets. Part of the product is lost since it is deposited on the surfaces of the premises. Another part is deposited in liquid form on the plant products. The product is not effective in this form. Only that fraction of the product which converts to vapour is effective, but it is extremely difficult to control the vapour concentration of the product. Again, the consumption of volatile biocidal and/or plant-protection product is much higher than with cold evaporation.

With the process of the invention, evaporation is cold evaporation which allows excellent control over the vapour concentration of product in the inner atmosphere of the premises. This concentration can be held at a high level, close to saturation if necessary, to maximize the effect of the product. Consumption of the volatile biocidal and/or plant-protection product is moderate compared with thermal fogging or hot evaporation since the total quantity of biocide exerts its action.

Product consumption is self-regulated. The biocidal and/or plant-protection product being vaporized at ambient temperature, lower than 50° C., it evaporates until it reaches no more than atmosphere saturation without any risk of supersaturation. Once this maximum has been reached, evaporation comes to a natural stop without any external action even if the evaporation device continues to operate.

Treatment efficacy is also due to the fact that the product vapour concentration in the atmosphere is held at a high level for a significant so-called saturation time, this saturation time being longer than 12 hours. Treatment can be applied either by rapidly injecting a large amount of product, or by spacing out injections so as to maintain the high concentration for sufficient time to guarantee efficacy.

Three preferred application modes have therefore been envisaged, based either on the principle of an impact effect with a product vapour concentration close to saturation concentration for a short period, or a lower concentration for longer periods. The efficacy of these products is dependent on the air concentration and contact time with the plant product.

The first application mode is via single injection, the vapour concentration of the or of each product in the inner atmosphere of the premises being held at between 50 and 100% of saturation concentration for a time of between 12 and 240 hours to obtain an effect of complete sterilization of the plant products.

The second application mode is the maintaining of a lower vapour concentration of the or of each product in the inner atmosphere of the premises throughout most of or substantially the entire storage period, at between 10 and 50% of saturation concentration.

In a third application mode, injections of the same type as in the first application mode are periodically performed, either when an increased risk has been visually ascertained or in accordance with a predetermined programme e.g. 5 injection days every month of storage.

For these three application modes, control over the injected quantity can be obtained in different manners.

According to a first method, control over the injected quantity is obtained by leaving evaporation to stop naturally, when saturation of the inner atmosphere of the premises has been reached. The amount of evaporated liquid is dependent on the quantities of air and liquid placed in contact and on the contact surface of the evaporation device.

According to a second method, control over the injected quantity is obtained by following a predetermined operating programme indicating the operating time per day and the amount of evaporated liquid per unit volume of the premises during said operating time.

According to a third method, the concentration of the or of each product in air is analysed, the injection device being driven by using the results of analysis, typically to maintain the concentration of the or of each product within a predetermined range.

The treatment process can also have one or more of the characteristics below, taken alone or in any technically feasible combination:
- at least one of the products is selected from the list of following biocidal or plant-protection products: essential oil; terpene; saturated or unsaturated C6 to C10 short chain alcohol e.g. octanol, 2-ethylhexanol; volatile synthetic product such as hexanal, dimethylnaphthalene and 3-decene-2-one; liquid organic acids with high boiling point such as pelargonic acid and parabenic acid; esters having biocidal action such as isoamyl isovalerianate;
- the premises contains plant products e.g. cereals stored for a storage time (DS) of generally more than one month;
- the treatment step comprises a continuous injection phase lasting more than 50% of the storage time (DS), preferably more than 75% of the storage time (DS) and further preferably more than 90% of the storage time;
- the treatment step comprises a single continuous injection phase having an injection time of 12 to 240 hours, or comprises several continuous injection phases separated by waiting phases without injection of biocidal and/or plant-protection product, each continuous injection phase having an injection time (DI) of between 12 hours and 240 hours;
- the liquid comprises several moderately volatile, biocidal and/or plant-protection products having respective vapour pressures differing from each other at ambient temperature;
- the respective vapour pressures of the volatile biocidal and/or plant-protection products extend over a pressure range of between $1.3 \times 10^{-5}$ bar and $4.10^{-3}$ bar;
- the inner atmosphere of the premises is heated during injection of the product vapour, to a temperature of between the normal temperature of the premises and the normal temperature plus 5° C.;
- the premises is a grain silo having an air inlet communicating with the outside and an air outlet communicating with the outside, the silo comprising forced ventilation provided to ensure circulation of air from the air inlet to the air outlet through the grains, the forced ventilation being switched off when injecting the or each biocidal and/or plant-protection product;
- the inner volume of the premises is larger than 200 m$^3$;
- the liquid is evaporated by contacting with a flow of air inside packing, the airflow containing the product vapours being injected into the premises;
- the premises is substantially airtight, the airflow circulating in the packing having a flow rate of between 1 and 10 m$^3$ per hour and per m$^3$ inner volume of the premises;
- the airflow circulating in the packing has a flow rate of between 1 and 6 m$^3$ per hour and per 100 m$^3$ inner volume of the premises.

In a second aspect, the invention concerns a treatment assembly, the assembly comprising:
- a liquid reservoir containing at least one moderately volatile biocidal and/or plant-protection product or product mixture having a boiling point of between 150 and 280° C.;
- a device to evaporate the liquid stored in the reservoir and to inject the evaporated liquid into the inner atmosphere of the premises, the evaporation device being configured to evaporate the liquid at a temperature lower than 50° C.;
- a controller to control the evaporation device, configured so that the vapour concentration of the or of each product in the inner atmosphere of the premises is maintained at more than 10% of the vapour saturation concentration of said product in said atmosphere for a saturation time of more than 12 hours.

The treatment assembly can also have one or more of the characteristics below, taken alone or in any technically feasible combination:
- at least one of the products is selected from the following list of biocidal or plant-protection products: essential oil; terpene; saturated or unsaturated C6 to C10 short chain alcohol e.g. octanol, 2-ethylhexanol; synthetic volatile product such as hexanal, dimethylnaphthalene and 3-decene-2-one; liquid organic acids having a high boiling point such as pelargonic acid and parabenic acid, esters having biocidal action such as isoamyl isovalerianate;
- the premises contains plant products e.g. potatoes stored for a storage time of more than one month, the controller being configured to carry out a continuous injection phase having an injection time of more than 50% of the storage time, preferably more than 75% of the storage time and further preferably more than 90% of the storage time;
- the premises contains plant products e.g. cereals, the controller being configured to carry out a single continuous injection phase having an injection time of 12 to 240 hours, or several continuous injection phases separated by waiting phases without injection of biocidal and/or plant-protection product, each continuous injection phase having an injection time of 12 to 240 hours;
- the liquid comprises several moderately volatile, biocidal and/or plant-protection products having respective vapour pressures differing from each other;
- the respective vapour pressures of the moderately volatile, biocidal and/or plant-protection products extend over a pressure range of between $1.3 \times 10^{-5}$ bar and $4.10^{-3}$ bar;

the treatment assembly comprises heating of the inner atmosphere of the premises, configured to heat said inner atmosphere during injection of the product vapour, to a temperature of between the normal temperature of the premises and the normal temperature plus 5° C.;

the evaporation device comprises an evaporator with packing in which the liquid is evaporated by contacting with a flow of air inside said packing, the evaporator being configured to inject the airflow containing the product vapours into the premises.

In a third aspect, the invention concerns a storage assembly for plant products, the storage assembly comprising:

premises preferably containing plant products; and a treatment assembly such as previously described, configured to inject the evaporated liquid into the inner atmosphere of the premises.

The storage assembly may also have one or more of the characteristics below taken alone or in any technically feasible combination:

the inner volume of the premises is larger than 200 m$^3$;

the premises is substantially airtight, the treatment assembly comprising an evaporator with packing in which the liquid is evaporated by contacting with a flow of air inside said packing, the evaporator being configured to inject the airflow containing the product vapours into the premises, the controller being programmed so that the airflow circulating in the packing has a flow rate of between 1 and 10 m$^3$ per hour and per m$^3$ inner volume of the premises;

the premises is a grain silo having an air inlet communicating with the outside and an air outlet communicating with the outside, the silo comprising forced ventilation provided to ensure circulation of air from the air inlet to the air outlet through the grains, the forced ventilation able to be switched off when injecting the or each biocidal and/or plant-protection product, the controller being programmed so that the airflow circulating in the packing has a flow rate of between 1 and 6 m$^3$ per hour and per 100 m$^3$ inner volume of the premises.

BRIEF DESCRIPTION OF THE DRAWINGS

Other characteristics and advantages of the invention will become apparent from the description below given for indication purposes only and in no way limiting, with reference to the appended Figures which include:

FIG. 2 is a simplified schematic illustration of a storage assembly conforming to a second embodiment of the invention.

DETAILED DESCRIPTION

Figure 1:
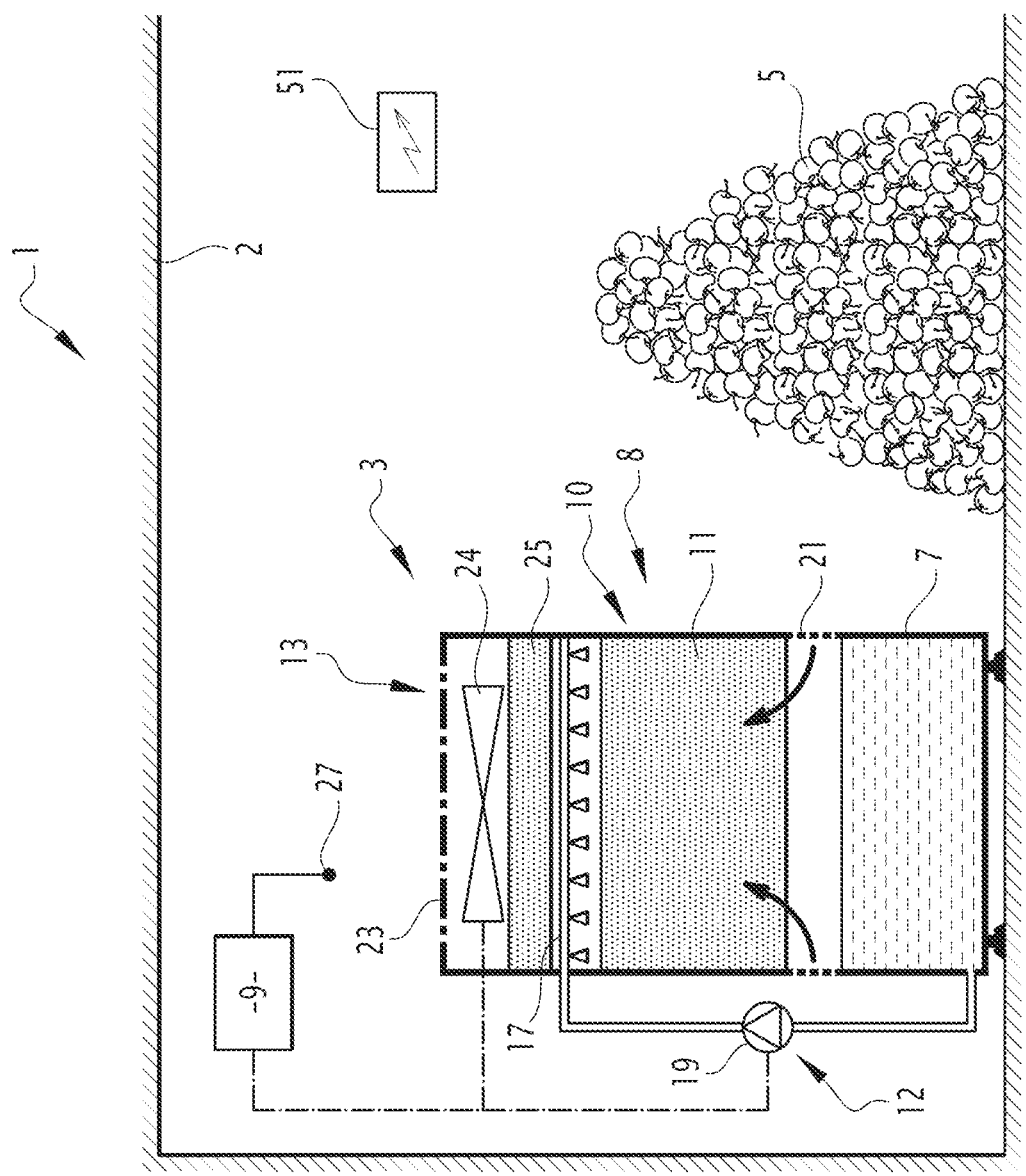
FIG. 1 is a simplified schematic illustration of a storage assembly conforming to a first embodiment of the invention.

The storage assembly illustrated in FIG. 1 comprises premises 2 and a treatment assembly 3.

The treatment assembly 3 is configured to evaporate a liquid containing at least one moderately volatile, biocidal and/or plant-protection product and to inject the evaporated liquid into the inner atmosphere of the premises 2.

The treatment is disinfection treatment and/or plant protection treatment.

In the first embodiment, the premises is substantially airtight. The premises is a closed enclosure in that exchanges between the premises atmosphere and the outside are reduced, in particular gas exchanges, for example so as not to jeopardize preservation of the plant products stored therein.

If the treatment is disinfectant treatment, the premises is storage intended for plant products for example, but not containing any plant products at the time of treatment. As a variant, the room is part of a hospital, school, industrial installation, or any other type of premises. It may be a vessel, a storage or transport tank, or any other type of enclosure to be disinfected.

For plant protection treatment, the room may be a chamber, greenhouse or any premises intended for the storage of plant products such as cereal grains, fruit or vegetables. Said premises is illustrated in FIG. 1. The treatment is applied when the plant products 5 are stored therein. As a variant, it is applied when the premises is empty.

The treatment assembly 3 is especially intended to treat the atmosphere of large volume storage. This volume is typically larger than 200 m$^3$, preferably larger than 500 m$^3$ and more preferably larger than 1000 m$^3$.

The treatment assembly 3 comprises:

a reservoir 7 to store a liquid containing at least one moderately volatile, biocidal and/or plant-protection product having a boiling point of between 150 and 280° C., preferably between 150 and 260° C.;

a device 8 to evaporate the liquid stored in the reservoir 7 and to inject the evaporated liquid into the inner atmosphere of the premises 2, the evaporation device 8 being configured to evaporate the liquid at a temperature lower than 50° C., a controller 9 to control the evaporation device 8.

The evaporation device 8 preferably comprises an evaporator 10 with packing 11 in which the liquid is evaporated via contacting with a flow of air within said packing 11.

The evaporator 10 is configured to inject the airflow containing the product vapours into the premises 2.

The evaporation device 8 further comprises:

a device 12 to inject a flow of the liquid into the packed evaporator 10;

a member 13 to circulate the airflow within the packed evaporator 10.

The evaporator is of an adapted type. For example, the evaporator is a packed tower of vertical axis in the illustrated example.

By packing it is meant here any type of structure allowing a large contact surface to be obtained between a liquid phase and a gas phase, and thereby improving exchanges between the liquid phase and gas phase.

The packing can therefore be packing of bulk type or packing of structured type.

In the case here, the packing is of Raschig ring or Pall ring type, or a honeycomb-structured packing.

It is typically made of a plastic material.

With the contacting, it is possible to obtain particularly efficient transfer between the flow of liquid and flow of air.

Advantageously, the evaporation device is placed in the premises. The circulation member 13 directly aspirates the inner atmosphere of the storage space and causes it to circulate in the packing, this atmosphere therefore forming the airflow.

Here the storage atmosphere corresponds to the volume of gas filling the premises and optionally bathing the plant products.

This atmosphere typically comprises air, and optionally the gases and products released by the plant products on maturing. It also comprises water vapour.

As a variant, the atmosphere is a modified atmosphere, the air being depleted of oxygen for example. This is the case in particular for the storage of some plant products such as apples.

The reservoir 7 is typically a vat placed vertically underneath the packing 11.

The injection device 12 is arranged to inject the liquid above the packing 11.

For this purpose, it typically comprises one or more spray ramps 17 positioned above the packing and a transfer member 19 such as a pump aspirating the liquid from the reservoir 7 and directing it into the ramp or ramps 17.

The circulation device 13 is arranged to create upward-moving circulation of air inside the evaporator 10.

To achieve this, the evaporation device 8 comprises one or more atmosphere inlets 21 leading to inside the evaporator 10 underneath the packing.

Each inlet 21 is in fluid communication with the inside of the premises 2.

The evaporation device 8 has an outlet 23 for the atmosphere loaded with evaporated liquid, positioned in the top part of the evaporator 10 above the packing 11. The outlet 23 is in fluid communication with the inside of the premises 2.

The circulation device 13 comprises a circulation member 24 such as a fan or blower for example positioned above the packing 11, typically at the top of the evaporation device 10.

The circulation member 24 aspirates the atmosphere loaded with evaporated liquid above the packing 11 and directs the same into or towards the outlet 23.

Preferably, the evaporation device 8 comprises a droplet separator 25, positioned above the spray ramps 17 and more specifically between the spray ramps 17 and the circulation member 24.

In one example of embodiment, the evaporation device 8 has a substantially constant, square horizontal cross-section of 700×700 mm. The reservoir 7 has the same horizontal cross-section and has a height of between 500 and 700 mm. The device has four inlets 21, each arranged on one of the sides. The height of the packing 11 is about 1 m. For example, the packing is placed 700 mm below the liquid inlet, the droplet separator 25 being positioned 300 mm above the liquid inlet.

The treatment assembly 1 preferably comprises a sensor 27 to measure the concentration of moderately volatile, biocidal and/or plant-protection product in the atmosphere, the controller 9 receiving information from the sensor 27.

The controller 9 is programmed to drive the injection device 12 and/or circulation member 24.

For example, the controller is a computer or computer part. As a variant, the electronic controlling device 29 is in the form of programmable logic components (FPGA, Field-Programmable Gate Array) or in the form of a dedicated integrated circuit (ASIC, Application Specific Integrated Circuit). The electronic device 29 is programmed to carry out a treatment strategy.

If the product is a biocidal product, the treatment is intended to sanitize the storage space.

If the product is a plant-protection product, also called plant health product, the treatment is intended to protect the plant products by preventing the development of disease and/or rotting and by eliminating insects, fungi and parasites, in particular fungi causing mycotoxins.

The liquid only contains biocidal products, or only contains plant-protection products, or it may comprise one or more biocidal products mixed with one or more plant-protection products.

At least one of the products is selected from the following list: essential oil; terpenes; saturated or unsaturated C6 to 010 alcohol e.g. octanol, 2-ethylhexanol; synthetic volatile products e.g. hexanal, dimethylnaphthalene and 3-decene-2-one; liquid organic acids with high boiling point e.g. pelargonic acid and parabenic acid, esters having biocidal action e.g. isoamyl isovalerianate.

For example, the essential oil is selected from the group formed by spearmint oil, clove oil, rose oil, thyme oil, oregano oil, eucalyptus oil, pine oil, cinnamon oil. As a variant, the liquid comprises one of the constituents of these oils selected from the group formed by L-carvone, eugenol, geraniol, thymol, carvacrol, eucalyptol, pinene, cinnamaldehyde.

Each biocidal and/or plant-protection product typically has a vapour pressure of between 0.01 mmHg and 3 mmHg, i.e. between 1.3 and 400 Pa.

Typically, the liquid only comprises the product or products without solvent or additive. As a variant, the liquid contains an aqueous or organic solvent in which the product(s) and one or more additives are dissolved. For example, the aqueous solvent is water. The organic solvent for example is a solvent of the type described in FR 2 791 910 or glycols, di-glycols and related esters. The additives for example are substances able to convey the active substance(s) or capable of providing a dilution effect.

At all events, the liquid at the contacting step is vaporized at a temperature lower than 50° C., preferably lower than 20° C., particularly between −2° C. and +12° C., and more particularly at between 0 and 10° C. For example, the liquid is evaporated at ambient temperature.

The controller 9 is configured so that the product vapour concentration in the inner atmosphere of the premises 2 is held at more than 10% of the saturation concentration of the vapour of said product in said atmosphere for a saturation time of more than 12 hours.

Preferably, the controller 9 is configured so that product vapour concentration in the inner atmosphere of the premises 2 is held at more than 30% of the saturation concentration of the vapour of said product in said atmosphere for a saturation time of more than 12 hours, preferably held at more than 50% or further preferably more than 80% and ideally more than 90% saturation.

The saturation concentration of each product is a function of the product and of the temperature in the premises. It corresponds to the maximum concentration possible of product vapour in the atmosphere, no additional evaporation of product being possible once saturation is reached, at constant temperature.

The saturation time is equal to the sum of all the periods during which the concentration remains higher than the targeted limit, namely 10% of saturation concentration, or 30% or 50% or 80% or 90%. This duration is continuous or divided into several periods separated by periods during which the product vapour concentration is lower than the targeted limit.

Preferably, the saturation time is more than 2 days per month, further preferably more than 5 days per month.

Controlling can be obtained in different manners.

In a first variant, the controller 9 sets the evaporation device 8 in continuous operation. The vapour concentration of the biocidal and/or plant-protection product or product mixture in the premises increases rapidly until it reaches saturation. Evaporation then stops naturally although the evaporation device continues to operate. Only small quantities of products are evaporated compensating for absorption by the plant products and leakage outside the premises.

The vapour concentration of the biocidal and/or plant-protection product or product mixture is permanently held close to 100% saturation.

In a second variant, the controller 9 is programmed to adjust the flow rate of liquid as a function of the concentration measured by the sensor 27. Preferably, it also drives the circulation member 24 in the same manner. It therefore controls the amount of evaporated biocidal and/or plant-protection product to maintain the concentration of product vapour measured by the sensor 27 in conformity with a pre-programmed time diagram corresponding to the desired treatment strategy. The time diagram indicates the desired changes in concentration of product vapour as a function of time.

In a third variant, the controller 9 is programmed to adjust the flow rate of liquid as a function of a pre-programmed time diagram corresponding to the desired treatment strategy. Preferably, it also controls the circulation member 24, in the same manner. The controller 9 therefore controls the amount of evaporated biocidal and/or plant-protection product in accordance with the pre-programmed time diagram. The latter indicates the desired changes in quantity of product vapour to be evaporated as a function of time.

Several application modes are envisaged as indicated above.

According to the first application mode, the controller 9 is configured to carry out a single vapour injection phase of the or of each product, a concentration of between 50 and 100% saturation concentration being maintained in the inner atmosphere of the premises continuously for a time of between 12 and 240 hours to obtain complete sterilization of the plant products or storage space. The period of time is preferably between 24 hours and 120 hours, more preferably between 24 hours and 72 hours. The targeted concentration is preferably more than 70% and further preferably more than 90% saturation.

In this application mode, the time diagram comprises a single slot of short duration.

According to a second application mode, the controller 9 is configured to carry out a single continuous injection phase.

If the premises contains plants products e.g. potatoes stored for a storage time DS, the continuous injection phase typically lasts an injection time DI longer than 50% of the storage time DS, preferably longer than 75% of the storage time DS, and further preferably longer than 90% of the storage time DS.

Typically, the storage time is longer than one month and is between one and 9 months for example.

In this application mode, the time diagram comprises a single continuous slot of long duration. The vapour concentration of the or of each biocidal and/or plant-protection product in the inner atmosphere of the premises is held at between 10 and 50% saturation substantially throughout the entire injection time.

According to a third application mode, the controller 9 is configured to carry out several continuous injection phases separated by waiting phases without injection of biocidal and/or plant-protection product.

Each continuous injection phase is of the type described for the first application mode. It has an injection time DI of between 12 hours and 240 hours, preferably between one day and five days. The vapour concentration of the or of each biocidal and/or plant-protection product is therefore maintained in the inner atmosphere of the premises at between 50% and 100% saturation at each injection phase for a saturation time longer than 12 hours and preferably of between one day and five days.

The waiting phases last a time of between 10 days and 2 months for example, preferably between 20 days and 40 days, and typically have a length of 30 days less the duration of the injection phase.

The injection phases typically all have the same duration. Similarly, the waiting phases typically all have the same duration.

As a variant, the injection phases and/or waiting phases have differing time periods.

With this strategy, the time diagram comprises several successive slots.

The quantities of each biocidal and/or plant-protection product evaporated at each injection phase, and the duration of each injection phase, are selected for rapid reaching of the targeted vapour concentration limit, and so that this concentration is maintained for sufficient time to obtain the desired biocidal and/or plant-protection effect.

The duration of each waiting phase is chosen to be sufficiently short so that disease, rotting, insects, fungi or parasites are unable to undergo significant development before the following injection phase.

As indicated above, a new injection phase is decided when an increase in risk has been visually ascertained. As a variant, the injection and waiting phases follow a predetermined programme e.g. 5 days of injection every storage month followed by 25 days without injection.

The invention therefore sets out to obtain rapid reaching of the targeted limit of vapour concentration. It is thereby sought to obtain perfect treatment of the premises and contents thereof by saturating the atmosphere very rapidly, the product vapour having immediate and optimum effect at every point of the premises.

This effect is able to be obtained since the contact surface between the liquid and atmosphere is extensive due to the presence of the packing. The treatment assembly of the present invention provides a contact surface between gas and liquid that can range up to 300 $m^2$ for example.

This allows the use of very fast air flow and liquid flow rates.

If the premises 2 is substantially airtight, the airflow circulating in the packing 11 has a flow rate of between 1 and 10 $m^3$ per hour and per $m^3$ of inner volume of the premises, preferably between 5 and 10 $m^3$ per hour and per $m^3$ of inner volume of the premises.

The flow rate of liquid in the packing 11 is typically between 1 and 30 $m^3/h$.

It is therefore possible to evaporate large amounts of product e.g. 20 litres of product per day, and quickly reach the saturation concentration of the product in the atmosphere.

As a variant, the packed evaporator is replaced by the machine sold under the trade name XEDAVAP, subject of the patent application filed under number FR1255999. In said machine, the liquid to be evaporated is injected onto a canvas through which an airstream is passed. The canvas has a developed surface area of between 1 $m^2$ and 4 $m^2$. The airflow rate is between 1000 and 3000 $m^3/hour$. With said machine it is possible to evaporate between 0.1 and 10 litres of liquid per day e.g. 1.2 litre/day of spearmint oil. Said machine is designed for smaller storage spaces than the packed evaporator.

The operation of the treatment assembly with a packed evaporator is the following.

The liquid to be evaporated is placed in the reservoir 7. The transfer member 19 directs the liquid into the ramp or ramps 17 which spray the liquid towards the packing 11. The atmosphere circulating member 24 creates an upward moving gas flow. The atmosphere enters into the treatment device 8 via the inlets 21, circulates upwards through the packing 11. The liquid circulates downwards through the packing 11, part of the liquid being evaporated in contact with the gas flow and entrained together with the atmosphere in vapour form. That fraction of liquid that is not evaporated falls back into the reservoir 7. It is recycled. The atmosphere loaded with evaporated liquid passes through the droplet separator 25 and is directed by the circulation member 24 towards the outlet 23.

The treatment assembly 8 discharges this vapour loaded atmosphere directly into the storage, via the outlet 23.

For example, the liquid flow rate is 3 $m^3$/hour, and the air flow rate about 2000 $m^3$/hour.

The invention also concerns a treatment process with at least one moderately volatile, biocidal and/or plant-protection product having a boiling point of between 150 and 280° C.

The process comprises a treatment step at which a liquid containing a biocidal and/or plant-protection product or product mixture is evaporated and injected into the inner atmosphere of premises 2, the liquid being evaporated at a temperature lower than 50° C.

The concentration of product vapour in the inner atmosphere of the premises 2 is held at more than 10% of the vapour saturation concentration of the product in said atmosphere for a saturation time of 12 hours or longer.

The product or products are of the type described above in connection with the treatment assembly.

The premises typically comprises plant products e.g. cereals stored for a storage time DS of more than one month, or plants in a greenhouse.

According to a first application mode, the treatment step comprises a single injection of the vapour of the product or product mixture, the concentration of the or of each product in the inner atmosphere of the premises being maintained at between 50 and 100% saturation concentration for a time of between 12 and 240 hours, to obtain a total sterilization effect of the plant products.

According to a second application mode, the treatment step comprises a single injection, a lower vapour concentration of the product or product mixture of between 10 and 50% the saturation concentration, being maintained in the inner atmosphere of the premises for most and even substantially the entire storage period.

According to a third application mode, the treatment step comprises several injections of same type as in the first application mode, performed periodically, either when an increase in risk has been visually ascertained or in accordance with a predetermined programme e.g. 5 injection days every storage month.

These treatment modes are as described above in connection with the treatment assembly.

The premises has an inner volume of more than 200 $m^3$. It is of the type described above in connection with the treatment assembly.

Advantageously, the liquid is evaporated by contacting with a flow of air inside packing 11, the airflow containing the product vapours being injected into the premises 2.

The liquid is preferably evaporated in an evaporation device of the type described above in connection with the treatment assembly.

In the first embodiment, the premises 2 is substantially airtight, the flow of air circulating in the packing having a flow rate of between 1 and 10 $m^3$ per hour and per $m^3$ of inner volume of the premises.

According to a first variant, the device used to evaporate the liquid operates continuously. The vapour concentration of the or of each biocidal and/or plant-protection product in the premises rapidly increases until it reaches saturation. Evaporation then stops naturally although the evaporation device continues to operate. The vapour concentration of the or of each biocidal and/or plant-protection product is permanently held close to 100% saturation.

According to a second variant, the quantity of evaporated biocidal and/or plant-protection product follows a pre-programmed time diagram, corresponding to the desired treatment strategy. This indicates the desired schedule for the amount of product vapour to be evaporated as a function of time.

According to a third variant, the vapour concentration of the or of each product in the atmosphere of the premises is permanently measured. The quantity of evaporated biocidal and/or plant-protection product is chosen to maintain the product vapour concentration measured by the sensor 27 in conformity with a pre-programmed time diagram, corresponding to the desired treatment strategy. The time diagram indicates the desired schedule for product vapour concentration as a function of time.

The process is designed to be implemented by the treatment assembly 8 described above. Conversely, the above-described treatment assembly 8 is particularly adapted for implementation of the process.

A second embodiment of the storage assembly of the invention will now be described with reference to FIG. 2. Only the points in which the second embodiment differs from the first will be detailed below. Elements that are the same or ensure the same functions will be designated with the same references in both embodiments.

In the second embodiment, the premises 2 is a grain silo having an air inlet 41 communicating with the outside and an air outlet 43 communicating with the outside.

The silo comprises forced ventilation 45 provided to ensure circulation of air from the air inlet 41 to the air outlet 43 through the grains 47.

Forced ventilation 45 is provided to ensure drying and/or cooling of the grains 47.

An air distribution collector 49 is arranged in the silo 2 underneath the grains. The forced ventilation 45 comprises an air circulating member 53 such as a fan with intake connected to the air inlet 41 and discharge connected to the collector 49.

The air outlet 43 is typically positioned in the upper part of the silo.

Under normal operation, the circulation member 51 draws in outside air, discharges this air into the collector 49, the air circulating from the collector 49 as far as the air outlet 43 through the grains 47.

The forced ventilation 45 is able to be switched off during injection of the or of each biocidal and/or plant-protection product.

The evaporation device 8 is positioned outside the silo 2. It is arranged to draw in outside air and to direct air loaded with product vapours from an area close to the air inlet 41 towards the air outlet 43.

For example, injection takes place in the lower part of the chamber holding the grains 47, in the collector 49.

Injection is carried out at low airflow rate.

For example, the airflow circulating in the packing 11 has a flow rate of between 1 and 6 $m^3$ per hour and per 100 $m^3$ inner volume of the premises, preferably between 2 and 4 m³ per hour and per 100 m³ inner volume of the premises.

The flow rate of liquid in the packing 11 is typically between 10 and 20 ml/m³ air. The injected air has a vapour concentration of the or of each biocidal and/or plant-protection product of more than 50% the saturation concentration of the vapour of said product in air, preferably more than 80% saturation and further preferably of more than 90% saturation.

The vapour of the or of each product is heavier than air and tends to accumulate at the bottom of the silo.

The vapour is driven towards the air outlet 43 by the airflow arriving continuously from the evaporation device 8. After a period of silo filling with the vapour of the or of each product, the vapour concentration is maintained in the silo above the desired limit, allowing continuous contact between the vapour and the grains. This extended contact leads to the desired biocidal and/or plant-protection effect.

Preferably, netting 51 is positioned at each air outlet of the silo so that, after treatment of the grains, no insects present are able to escape and contaminate other parts of the installation. This netting is chosen to allow air to pass but to block insects.

The treatment process corresponding to the second embodiment of the storage assembly will now be described. Only those points in which the process differs from the one in the first embodiment of the storage assembly will be detailed below. Same elements or elements ensuring the same functions will be designated with the same references.

In this process, the forced ventilation 45 of the silo is switched off during the injection of the or of each biocidal and/or plant-protection product.

The airflow circulating in the packing 11 of the injection device 8 has a flow rate of between 1 and 6 m³ per hour and per 100 m³ inner volume of the premises.

The treatment strategy is of the type in which the treatment step either comprises a single continuous injection phase, or comprises several continuous injection phases separated by waiting phases without injection of biocidal and/or plant-protection product. In both cases, each continuous injection phase has an injection time DI of more than 12 hours.

Typically, each injection phase lasts between one and 15 days, preferably between two and 5 days.

In one variant, applicable to all embodiments, the liquid comprises several moderately volatile, biocidal and/or plant-protection products having respective vapour pressures differing from each other at ambient temperature.

Advantageously, the respective vapour pressures of the volatile biocidal and/or plant-protection products at ambient temperature extend over a pressure range of $1.3 \times 10^{-5}$ bar and $4.10^{-3}$ bar.

Since the applicant has observed that there exists an optimum range of vapour pressure to obtain the maximum desired biocidal and/or plant-protection action, it is considered that a vapour pressure of the ideal liquids must lie within between 0.01 and 3 mmHg ($1.3 \times 10^{-5}$ bar and $4.10^{-3}$ bar) at ambient pressure. If the vapour pressure is too low, the products evaporate slowly and the vapour concentration in the inner atmosphere of the premises cannot reach a sufficient value to obtained the desired effect. If the vapour pressure is too high, there can occur major losses to outside the premises.

By using several products having stepped vapour pressures, it is possible to remain within the desired vapour pressure range over a broad temperature interval around ambient temperature and to obtain a larger spectrum of activity compared with the activity of each product taken alone.

In one variant, applicable to all embodiments, the treatment assembly 8 comprises heating 51 to heat the inner atmosphere of the premises 2. This heating is configured to heat said inner atmosphere, during injection of the product vapour, to a temperature of between the normal temperature of the premises 2 and the normal temperature plus 5° C.

The normal temperature is the temperature of the premises 2 in the absence of treatment.

The temperature is increased during the injection phases to increase the saturation concentration of the vapour of the or of each product. It is therefore possible to increase the vapour concentration of the or of each product, leading to greater efficacy of the treatment. The normal temperature value is restored by switching off the heating during the waiting phases without vapour injection.

The invention claimed is:

1. A method of treatment of plant products stored in premises or sanitization of the premises, comprising:
   evaporating and injecting at least one biocidal or plant-protection product having a boiling point between 150 and 280° C. into an inner atmosphere of the premises, the biocidal or plant protection product being evaporated at a temperature lower than 50° C., the vapor concentration of the biocidal or plant protection product in the inner atmosphere of the premises being held at more than 10% of a saturation concentration of the vapor of said biocidal or plant protection product in said atmosphere at said temperature for a saturation time of more than 12 hours;
   wherein the premises have an inner volume of more than 200 m³;
   wherein the at least one biocidal or plant-protection product is evaporated by circulating a liquid containing the at least one biocidal or plant-protection product in a packed tower containing a packing, a flow of the liquid being injected into the packed tower, a flow of air being circulated into the packed tower, the flow of liquid and the flow of air flowing through the packing, the flow of liquid contacting the flow of air within said packing, the flow of air containing vapors of the at least one biocidal or plant-protection product being injected into the premises.

2. The method according to claim 1, wherein the at least one biocidal or plant protection product comprises essential oil.

3. The method according to claim 1, wherein the premises contain plant products, stored for a storage time.

4. The method according to claim 3, wherein the injecting comprises a continuous injection phase lasting more than 50% of the storage time, during which the vapor concentration in the atmosphere is held at between 10% and 50% of saturation.

5. The method according to claim 1, wherein the injecting comprises a single continuous injection phase having an injection time of 12 to 240 hours, or comprises several continuous injection phases separated by waiting phases without injection of biocidal or plant-protection product, each continuous injection phase having an injection time of between 12 and 240 hours, the vapor concentration in the atmosphere being held at between 50% and 100% saturation during the or each injection phase.

6. The method according to claim 1, wherein the at least one biocidal or plant protection product comprises a plurality of biocidal or plant-protection products having respective vapor pressures differing from each other at ambient temperature.

7. The method according to claim 6, wherein the respective vapor pressures of the biocidal or plant-protection products extend over a pressure range of between $1.3 \times 10^{-5}$ bar and $4.10^{-3}$ bar.

8. The method according to claim 1, wherein the premises comprise a grain silo having an air inlet communicating outside the silo and an air outlet communicating outside the silo, the silo comprising a forced ventilation designed to ensure circulation of air from the air inlet to the air outlet through any contents of the silo, the forced ventilation being switched off during injection of the or of each biocidal or plant protection product.

9. The method according to claim 1, wherein the packed tower has a vertical axis.

10. The method according to claim 1, wherein the packing is of bulk type or of structured type.

11. The method according to claim 1, wherein a reservoir containing the liquid is placed vertically underneath the packing, the liquid being aspired from the reservoir and sprayed above the packing.

12. The method according to claim 11, wherein the liquid is sprayed by one or more spray ramps positioned above the packing.

13. The method according to claim 12, wherein a pump aspirates the liquid from the reservoir and directs the liquid into the one or more spray ramps.

14. The method according to claim 12, wherein a circulation device creates upward-moving circulation of the flow of air inside the packed tower, the air entering the packed tower through one or more atmosphere inlets leading into the packed tower underneath the packing.

15. The method according to claim 1, wherein the at least one biocidal or plant protection product is selected from the group consisting of:
   terpene; saturated or unsaturated C6 to C10 short chain alcohol; or esters having biocidal action.

* * * * *